(12) United States Patent
Zoeller et al.

(10) Patent No.: US 6,683,216 B1
(45) Date of Patent: Jan. 27, 2004

(54) CONTINUOUS PROCESS FOR THE PREPARATION OF AMINES

(75) Inventors: Joseph Robert Zoeller, Kingsport, TN (US); Norma Lindsey Buchanan, Kingsport, TN (US); Elizabeth Celia Sharkey, Jonesborough, TN (US); Daniel Latham Terrill, Kingsport, TN (US); Steven Paul Bellner, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/289,016

(22) Filed: Nov. 6, 2002

(51) Int. Cl.$^7$ ............................................. C07C 209/00
(52) U.S. Cl. ........................ 564/448; 564/414; 564/488
(58) Field of Search ................................ 564/448, 414, 564/488

(56) References Cited

U.S. PATENT DOCUMENTS

| 3,847,974 A | 11/1974 | Gruenstadt et al. |
| 4,590,292 A | 5/1986 | Blackwell et al. |
| 5,032,687 A | 7/1991 | Diehl et al. |
| 5,728,873 A | 3/1998 | Kleemiss et al. |

FOREIGN PATENT DOCUMENTS

| DE | 39 09 142 A1 | 10/1990 |
| GB | 1 257 097 | 8/1969 |

OTHER PUBLICATIONS

E.S. Wallis and J.F. Lane, *Org. Reactions*, 3, 267 (1946).

Henry W. Schiessel in *Kirk–Othmer Encyclopedia of Chemical Technology*, 4$^{th}$ ed., vol. 13, p. 560–605 (1995).

Vaidyananthan and Wilson, *J. Org. Chem.*, 54, (1989), 1815–1820.

Koizumi et al in *Kogyo Kagaku Zasshi* (1965), 68(1), 102–105 (Chem. Abstracts No. 62:90867).

*Primary Examiner*—Samuel Barts
(74) *Attorney, Agent, or Firm*—Eric D. Middlemas; Bernard J. Graves, Jr.

(57) ABSTRACT

Disclosed is a process for the preparation of amines by continuously feeding a carboxamide, aqueous alkaline hypohalite, and aqueous alkaline hydroxide to a first reaction zone to form a N-halocarboxamide, measuring the concentration of at least one reaction component in the effluent from the first reaction zone, and using the result of that measurement to control the feed rate of at least one of the feed components of to achieve at least 90% conversion of the carboxamide in the first reaction zone. The effluent from the first reaction zone is fed continuously to a second reaction zone where it further reacts to form an aqueous solution of an amine. The effluent from the second reaction zone may be fed continuously to a distillation column. The process is particularly useful for the preparation of cyclopropylamine.

18 Claims, 1 Drawing Sheet

Fig. 1

CONTINUOUS PROCESS FOR THE PREPARATION OF AMINES

FIELD OF THE INVENTION

This invention relates to a process for the preparation of amines. More specifically, this invention pertains to a continuous process for the preparation of amines by the reaction of alkaline hypohalites with carbox-amides.

BACKGROUND OF THE INVENTION

Amines are important intermediates for the preparation of liquid crystal polymers, agrochemical, and pharmaceutical compounds. Although many simple aliphatic and aromatic amines are available by efficient, low cost processes, such as reductive amination, displacement of halides with ammonia, or amination of alcohols, many synthetically difficult, hindered, or more reactive amines are prepared from their corresponding carboxamides by the Hofmann reaction. These more complex amines are especially useful in the production of agrochemical and pharmaceutical compounds. For example, cyclopropylamine is particularly useful as an agrochemical and pharmaceutical intermediate and is produced from cyclopropanecarboxamide by the Hofmann reaction.

The Hofmann reaction suffers from a number of disadvantages and often provides only moderate yields and selectivities. With complex and reactive carboxamides, for example, the Hofmann reaction is frequently subject to troublesome side reactions, such as hydrolysis of the carboxamide, overhalogenation, and formation of acyl ureas (see, for example, E. S. Wallis and J. F. Lane, *Org. Reactions,* 3, (1946), 267). To avoid these side reactions, it is often necessary to use expensive reagents, such as sodium methoxide, bromine, or phase transfer catalysts. These expensive reagents render the process uneconomical for commercial production. In addition, the Hofmann reaction is usually carried out in a complex, multistep process that is often not practical for the more efficient continuous mode of operation.

Several modifications of the Hofmann reaction have appeared in the patent literature that attempt to circumvent these problems. For example, U.S. Pat. No. 's. 4,590,292; 5,032,687; 5,728,873; and British Patent No. 1,257,097; describe process modifications to reduce hydrolysis of the starting carboxamide, first, by adding the hypochlorite at low temperature (<20° C.) to form the N-chlorocarboxamide intermediate, then by adding base to allow the rearrangement to proceed. Although this method of addition reduces hydrolysis of the carboxamide prior to chlorination, it can lead to the formation of acyl ureas which have low solubility and can cause plugging of process lines and equipment.

Many of the above-mentioned problems are exacerbated when the Hofmann reaction is conducted in a continuous reaction mode. For example, the formation of acyl urea by-products becomes especially troublesome in a continuous operation. This by-product is often insoluble in the reaction milieux and causes plugged process lines and valves. Maintaining the bleach to carboxamide ratio at optimum levels is important under continuous conditions. Incomplete conversion of the carboxamide and poor yields result if too little bleach is used. By contrast, too much bleach results in overchlorination to produce N-chloramines. These N-chloroamines subsequently may undergo decomposition, degradation to nitriles, or further reaction with the amine product to form hydrazines (see for example, Vaidyananthan and Wilson, *J. Org. Chem.,* 54, (1989), 1815. and Schiessel in *Kirk-Othmer Encyclopedia of Chemical Technology,* $4_{th}$ ed., vol.13 (1995), p. 560). In a continuous process, these dangerous and toxic materials may accumulate which presents health and physical hazards and makes purification of the desired product difficult.

Accurately controlling hypohalite concentrations is difficult because of the variability in concentration of commercial hypohalite and because of the instability of aqueous hypohalite solutions. As a consequence of this instability, the concentration of hypohalite continuously declines upon storage. Frequent analysis of the hypohalite solutions are required to insure that proper amounts are used. For a commercial process, such analytical requirements can be expensive and subject to errors that, in turn, cause operational delays and poor quality product.

There have been several processes that describe the operation of a Hofmann reaction to produce amines in a continuous or semi-continuous mode. German Patent Application No. 3,909,142 A2 discloses a continuous process for producing amines,.including cyclopropylamine, where an aqueous solution of sodium hydroxide and sodium hypochlorite is mixed with an aqueous solution of carboxamides in a tubular reactor operating at a temperature of 45 to 260° C. U.S. Pat. No. 3,847,974 discloses a continuous process utilizing a 2-stage reactor system to produce the intermediate N-chlorocarboxamide and to convert the N-chlorocarboxamide to the amine. Koizumi et al. in *Kogyo Kagaku Zasshi* (1965), 68(1), 102–105 (Chem. Abstracts No. 62:90867) disclose the preparation of 5-methyl-3-aminoisoxazole from 5-methylisoxazole-3-carboxamide using a continuous flow 3-stage stirred tank reactor. These processes do not provide a means to accurately measure and control the concentration of hypohalite and, hence, the extent of reaction. As a consequence, these processes are subject to operational and purification difficulties from the formation of side products. U.S. Pat. No. 5,728,873 describes a 2-stage, semicontinuous process wherein the reaction of cyclopropanecarboxamide with hypochlorite is conducted batchwise at a temperature range of 0–20° C. and then, the reaction product is subsequently fed continuously to a tubular reactor at a temperature range of 45–260° C. Although this process may avoid some of the problems associated with side reactions, its productivity is reduced because of the less efficient, semicontinuous mode.

As is evident from the processes described hereinabove, the known methods for the preparation of amines through the Hofmann reaction require multiple, complex processing steps to avoid side reactions. These processes are difficult to conduct in a continuous manner and thus operate with low space-time yields. Of the known continuous processes, none provide a method to operate the Hofmann reaction-in a selective manner that is generally applicable to a wide range of carboxamides.

BRIEF SUMMARY OF THE INVENTION

The present invention provides a process for the preparation of amines comprising the following steps:

I. continuously feeding a carboxamide reactant, an aqueous alkaline hypohalite reactant, and an aqueous alkaline hydroxide reactant to a first reaction zone wherein the carboxamide, hypohalite, and hydroxide react to form a first reaction mixture comprising a plurality of components wherein at least one of the components is an N-halo-carboxamide;

II. continuously removing the first reaction mixture from the first reaction zone;

III. measuring the concentration of at least one component in the first reaction mixture and using the result of that measurement to control the feed rate of at least one of the reactants of step I to achieve at least 90% conversion of the carboxamide in the first reaction zone; and IV. continuously feeding the first reaction mixture to a second reaction zone wherein the first reaction mixture further reacts to form a second reaction mixture comprising an aqueous solution of an amine.

Although a variety of reactor types may be used, a preferred embodiment of this invention is a continuous process wherein the first reaction zone comprises a tubular reactor which enables the conversion of the carboxamide to occur under substantially plug-flow conditions.

Another embodiment of the present invention is a continuous process wherein the measurement of components in the first reaction mixture is carried out using UV-Visible spectroscopy, infrared spectroscopy, or a combination thereof. Yet another embodiment of the present invention is a continuous process for the preparation of cyclopropylamines which comprises the steps of:

I. continuously feeding (i) an aqueous solution of a cyclopropanecarboxamide and (ii) a solution comprising sodium hypochlorite and sodium hydroxide to a first reaction zone comprising a tubular reactor, wherein the cyclopropanecarboxamide, sodium hypochlorite, and sodium hydroxide react to form a first reaction mixture comprising a N-chlorocyclopropanecarboxamide;

II. continuously removing the first reaction mixture from the first reaction zone;

III. measuring the concentration of the sodium hypochlorite in the first reaction mixture using UV-Visible spectroscopy and using the result of that measurement to control the feed rate of at least one of the solutions (i) or (ii) of step I to achieve at least 90% conversion of the cyclopropanecarboxamide in the first reaction zone; and IV. continuously feeding the first reaction mixture from the first reaction zone to a second reaction zone wherein the first reaction mixture further reacts to form a second reaction mixture comprising an aqueous solution of a cyclopropylamine.

A preferred embodiment of the present invention is a continuous process wherein cyclopropanecarboxamide is the carboxamide, and the second reaction mixture is fed continuously to a distillation column where cyclopropylamine is continuously recovered and purified. The present invention is suitable for the preparation of a wide range of amines and is especially useful for the preparation of cyclopropylamines. Our process provides for accurate control of reactant feeds and thus gives high yields and selectivities without many of the side reactions that often accompany the Hofmann reaction. In addition, our process is conducted in a continuous mode which affords high efficiency, stable operation, and consistent product quality.

DETAILED DESCRIPTION

The present invention provides a continuous process for the preparation of amines utilizing the Hofmann reaction of carboxamides with alkaline hypohalite. We have discovered that the Hofmann reaction may be carried out continuously in an efficient and economical manner by a process utilizing two reaction zones, measurement of the concentration of at least one of the components of a first reaction mixture from the first reaction zone, and using that measurement to control the feed rate of at least one reactant into the first reaction zone to achieve a desired conversion or concentration of a reaction component. The term "component" or "reaction component" as used herein, means any starting material, reactant, product, intermediate, solvent, or by-product present within the reaction mixture, any process stream, or within any process equipment. Non-limiting examples of components or reaction components which may be found in the first reaction mixture include solvents, one or more reactants, such as unreacted carboxamides and alkaline hypohalites; one or more intermediates such as N-halocarboxamides, isocyanates, and carbamates; one or more by-products which may be produced from the reaction of any combination of starting reactants, intermediates, or final product, including amines, carboxylic acids, halogenated amines, and ureas; and the final amine product. In one embodiment, the present invention involves (1) continuously feeding a carboxamide reactant, an aqueous alkaline hypohalite reactant, and an aqueous alkaline hydroxide reactant to a first reaction zone wherein the carboxamide, the hypohalite, and alkaline hydroxide react to form a first reaction mixture comprising a plurality of components wherein at least one of the components is an N-halocarboxamide; (2) continuously removing the first reaction mixture from the first reaction zone; (3) measuring the concentration of at least one component in the first reaction mixture and using the result of that measurement to control the feed rate of at least one of the reactants to achieve at least 90% conversion of the carboxamide in the first reaction zone; and (4) continuously feeding the first reaction mixture to a second reaction zone wherein the first reaction mixture further reacts to form a aqueous solution comprising an amine.

Many carboxamides are suitable as starting materials in our novel process. The terms "carboxamide", "carboxylic amide", "carboxylic acid amide", and "amide", as used herein, are synonymous and refer to amides of carboxylic acids. In general, carboxamides of the structure can be used wherein R is (i) a linear or branched alkyl, alkenyl, or alkynyl radical containing up to about 10 carbon atoms, (ii) a cycloalkyl or cycloalkenyl radical containing 3 to about 7 carbon atoms, (iii) a carbocyclic aromatic or heterocyclic aromatic radical which may carry one or more substituents, or (iv) a 5- or 6-membered non-aromatic heterocyclic radical comprising one or more hetero atoms selected from the group consisting of oxygen, nitrogen, phosphorus, and sulfur. Examples of alkyl, alkenyl, and alkynyl groups include, but are not limited to, methyl, ethyl, n-propyl, isopropyl, isobutyl, n-butyl, tertiary butyl, pentyl, hexyl, 2-ethylhexyl, octyl, decyl, vinyl, 1-propenyl, 1-butenyl, 1-pentenyl, 2-propynyl, 2-butynyl, 2-octenyl, and various isomers thereof. Examples of cycloalkyl and cycloalkenyl radicals include, but are not limited to, cyclopropyl, cyclobutyl, cyclobutenyl, cyclopentyl, cyclopentenyl, cyclohexyl, cyclohexenyl, cycloheptyl,

2-methylcyclopropyl, cycloheptenyl, 4-methylcyclohexyl, 3-methylcyclopentenyl, and the like. Examples of carbocyclic aromatic and heterocyclic aromatic radicals are phenyl, aryloxy, benzyl, tolyl, pyridyl, pyrrolyl, pyrimidinyl, pyrazinyl, indolyl, thiophenyl, thiazolyl and the like. Examples of non-aromatic heterocyclic radicals are tetrahydrofuranyl, tetrahydrothiofuranyl, phosphoranyl, imidazolidinyl, morpholinyl, and the like. The carboxamide can be added as a melt, or more preferably as an aqueous solution. Lower molecular weight carboxamides are water soluble and their aqueous solutions can be generated in a wide range of concentrations, especially if the water is heated. In the present invention, carboxamide concentrations in a range of about 5 weight % (weight % is abbreviated herein as "wt %") up to about 90 wt % in water are preferred. The more preferred carboxamide levels in water for this process, however, are in a range of about 10 wt % up to about 70 wt %, with about 15 wt % up to about 55 wt % being the most preferred range.

The process of the present invention may be conducted effectively with a variety of alkaline hypohalites. The term "alkaline hypohalite" as used in the present invention means any alkali or alkaline earth metal hypohalite. Examples of typical alkaline hypohalites are lithium hypochlorite, lithium hypobromite, sodium hypochlorite, sodium hypobromite, potassium hypochlorite, potassium hypobromite, calcium hypochlorite, and calcium hypobromite. The alkaline hypohalites that may be used for the reaction are available commercially from numerous sources or can be generated by addition of halogen, e.g., chlorine or bromine, to aqueous alkali or alkaline earth metal hydroxide solutions. For the present invention, hypohalite concentrations in a range of about 3 wt % up to about 17 wt % in water are preferred. A more preferred concentration range of hypohalite is about 10 wt % up to about 15 wt %. Because of its commercial availability and low cost, sodium hypochlorite is preferred. Solutions of hypohalite, particularly concentrated hypochlorite, are unstable over time and are generally stored cold.

The alkaline hydroxide can be introduced either as a solid or as an aqueous solution. The term "alkaline hydroxide" means any alkali or alkaline earth metal hydroxide or any alkali or alkaline earth metal compound that produces a basic (i.e., pH>7) solution when mixed with or dissolved into water. Suitable alkaline hydroxides include but are not limited to lithium hydroxide, sodium hydroxide, potassium hydroxide, and calcium hydroxide, calcium oxide, barium hydroxide, and barium oxide. The preferred form of the alkaline hydroxide is as an aqueous solution containing about 10 wt % up to about 50 wt % alkaline hydroxide. Sodium hydroxide is the preferred alkaline hydroxide because of its low cost and commercial availability in aqueous solution or in solid form.

The preferred molar ratio of alkaline hydroxide to alkaline hypohalite is about 2:1 with molar ratios in a range of about 2.1:1 to about 3:1 moles alkaline hydroxide:moles alkaline hypohalite being most preferred. These ratios of hydroxide to hypohalite serve to stabilize the hypohalite against decomposition and retard the formation of by-product acyl ureas. The carboxamide, alkaline hypohalite, and alkaline hydroxide may be introduced simultaneously as separate feed streams into the first reaction zone. Alternatively, the hydroxide and the carboxamide may be mixed before introduction into the first reaction zone, but the presence of hydroxide can lead to hydrolysis of the carboxamide. It is preferred to premix the alkaline hydroxide and alkaline hypohalite in a molar ratio of about 2:1 moles hydroxide-:hypohalite before introduction into the first reaction zone and feed this solution into the first reaction zone simultaneously with the aqueous solution of carboxamide. Premixing the hydroxide and hypohalite insures that the reaction will not drift below about 2:1 hydroxide:hypohalite ratio in the presence of the carboxamide. Alternatively, the hydroxide-hypohalite solution may be mixed continuously with the aqueous solution of carboxamide in several ways familiar to practitioners skilled in the art, including the use of a static mixer, an in-line stirrer, or a stirred vessel. A static mixer is especially preferred due to its. simplicity, rapid mixing, and short hold up time.

The process of the present invention is carried out wherein the temperature of first reaction zone is in a range of about 30° C. up to about 55° C. A more preferred temperature range for the first reaction zone is about 45° C. up to about 55° C. Within the first reaction zone, the reaction between the carboxamide and the hypohalite proceeds to an intermediate stage to give a product containing an N-halocarboxamide (1) but may also contain other reaction intermediates such as the corresponding isocyanate (2) or carbamate (3).

Pressures of about 0 kilopascals gauge up to about 2000 kilopascals gauge may be used as necessary to suppress boiling of the reaction mixture, if desired, within the first reaction zone.

The process of the present invention may utilize a variety of reactor types. Examples of suitable reactor types include, but are not limited to, stirred tank, continuous stirred tank, trickle bed, tower, slurry, and tubular reactors. It is preferred that the first reaction zone is a tubular reactor operated under substantially plug-flow conditions, i.e. conditions in which the carboxamide, alkaline hypohalite, and reactant feed solutions are continuously passed through a reactor packed as a singular mix, or "plug" with little or no backmixing such that the concentrations of reaction products in the effluent of the reactor are increased relative to the concentration of reaction products in the influent to the reactor.

A continuous stirred tank reactor is the preferred format of the second reactor zone. The second reaction zone is maintained at a temperature of about 60° C. up to about 1 50° C., more preferably about 70° C. to about 105° C., and a pressure of about 0 kilopascals up to about 2000 kilopascals gauge. Within the second reaction zone, the N-halocarboxamides and other intermediates, such as the corresponding isocyanates and carbamates, are converted to the corresponding amine. The pressure at which the second reaction zone is operated is not critical except that it is desirable to employ sufficient pressure to maintain the desired temperature of the reaction mixture by suppressing vaporization of the reaction components. If desired, the final amine reaction product may be purified by distillation from the second reaction zone.

The use of first and second reaction zones and their widely differing temperatures permit the measurement of the concentration of at least one component of the first reaction mixture by various analytical methods before the generation of amine progresses. Examples of reaction components that may be measured include the starting carboxamide, the hypohalite, and reaction intermediates such as the N-halocarboxamide, isocyanate, or carbamate corresponding to the starting carboxamide. The measurement can be carried out continuously using any rapid, reproducible analytical technique that has sufficient turnaround to enable a practical control system and that is compatible with the reaction components. Examples of useful analytical techniques include gas chromatography, liquid chromatography, UV-Visible spectroscopy, and infrared spectroscopy. Preferred. analytical techniques which provide rapid analysis of reaction components include UV-Visible spectroscopy, infrared spectroscopy, or a combination of UV-visible and infrared spectroscopy. For example, infrared spectroscopy may be utilized to observe the infrared bands or frequencies for the starting carboxamide or intermediate products, such as the N-halocarboxamide, or carbamate. Useful infrared absorption frequencies for several components present during the reaction of cyclopropanecarboxamide to cyclopropylamine using sodium hypochlorite and sodium hydroxide are provided in Table 1 as illustrative examples. Useful infrared absorption bands for other carboxamides are readily determined by practitioners skilled in the art. Similarly, UV-Visible spectroscopy may be used to detect reaction components by observation and measurement of the UV-Visible absorption bands. These absorption bands may be determined by techniques well known to persons skilled in the art.

TABLE 1

Infrared Absorption Bands for Selected Reaction Components in the Hofmann Reaction of Cyclopropanecarboxamide to Cyclopropylamine with Sodium Hydroxide and Sodium Hypochlorite

| Intermediate | Infrared Absorption Bands (cm$^{-1}$) |
| --- | --- |
| Carboxamide | 1656, 1604, 1465, 1445, 1303, 934 |
| N-halocarboxamide | 1541, 1451, 1938, 959 |
| Carbamate | 1566, 1477, 1455, 1324 |

A preferred analytical technique is UV-Visible spectroscopy which may be used for measurement of the hypohalite at wavelengths between 300 and 375 nm. Within this range of wavelengths, hypohalite concentrations in the range of about 0.01 wt % to about 0.02 wt % may be detected in the effluent from the first reaction zone.

When spectroscopic techniques are used, a probe is placed, for example, immediately at the outlet of the first reaction zone. Typically, the spectroscopic probe may be placed at a location where it may contact the effluent of the first reaction zone. This may be accomplished by several means such as placing the probe directly into the effluent stream or by utilizing a slipstream or by-pass in which a smaller portion of the first reaction mixture is contacted with the spectroscopic probe. Various designs for spectroscopic probes exist and are well known to practitioners skilled in the art. Non-limiting examples of spectroscopic probes are transmittance devices, which transmit light through a solution, and reflectance devices, which utilize internal reflectance phenomena where light reflects along a crystal surface to obtain spectra. In normal operation, the spectroscopic probe is connected to the spectrometer by fiber optic cables that allow remote measurement.

Another aspect of the present invention is to use the measurement of one or more components of the first reaction mixture to control the feed rate of at least one reactant to the first reaction zone to achieve at least a 90% conversion of the carboxamide to the intermediate N-halocarboxamide, carbamate, or isocyanate within the first reaction zone. The control of the hypohalite, hydroxide, or carboxamide addition rates is accomplished by using the results of the measurement of the reaction component to adjust the addition rates of the above reactants until the concentration of the reaction component reaches its desired level. For example, the feed rate of the carboxamide and/or hypohalite solution may be the adjusted to achieve a level of the starting carboxamide in the effluent from the first reaction zone indicative of at least 90% conversion of the starting carboxamide. Alternatively, the concentration of the intermediate N-halocarboxamide may be measured and used to control the feed rate of the either the starting carboxamide or the alkaline hypohalite solution to achieve a concentration corresponding to at least a 90% conversion of the starting carboxamide. It is preferred to control the hypohalite addition rate.

By the term "conversion" it is meant that a specified molar fraction of the carboxamide introduced into the reactor is reacted to form either the desired N-chlorocarboxamide or other reaction products. A "90% conversion", for example, means 90% of the carboxamide present in the feed to the reactor on a molar basis is reacted to products.

The preferred method is to measure the concentration of hypohalite with UV-Visible spectroscopy and control the carboxamide and/or hypohalite feeds. When using this technique, the bleach addition is controlled by adding hypohalite until a response is detected in the desired range of the spectrum (300–375 nm, preferably 325–350 nm) and adjusting the bleach as needed to maintain a detectable, but low response. Although the sensitivity of the bleach detection is dependent upon the path length of the UV-Visible cell used in the monitor, control within 0.01 to 0.02 wt % hypohalite in the effluent from the first reaction zone is normally achievable. Control of the feed rates may be accomplished either manually or electronically using techniques well known by those skilled in the art. For example, the feed rates may be controlled electronically by sending the signal from the detector of the UV-Visible or infrared spectrophotometer to a control computer which interprets the signal and adjusts the feeds to the first reaction zone based on a programmed algorithm. Such computers and control programs are readily available and well known to persons skilled in the art.

The present invention is particularly useful for the continuous preparation of cyclopropylamines from cyclopropanecarboxamides. In this embodiment, an aqueous solution of a cyclopropanecarboxamide and a solution comprising an alkaline hypohalite and an alkaline hydroxide are continuously fed to a first reaction zone which comprises a tubular reactor. The term "continuous" as used herein means a process wherein reactants are introduced and products withdrawn simultaneously in an uninterrupted manner. By "continuous" it is meant that the process is substantially or completely continuous in operation and is to be contrasted with a "batch" process. "Continuous" is not meant in any way to prohibit normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which no material is fed or removed into the reactor. The term "semicontinuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses.

The preferred hypohalite is sodium hypochlorite and the preferred hydroxide is sodium hydroxide. In a preferred embodiment, the cyclopropanecarboxamide reacts with the sodium hypochlorite within the first reaction zone to form an aqueous first reaction mixture which comprises N-chlorocyclopropanecarboxamide. The concentration of the sodium hypochlorite in the effluent from the first reaction zone may be measured using UV-Visible spectroscopy and the result of that measurement used to control the feed rate of the carboxamide solution, the hypochlorite solution or, possibly, both to achieve at least a 90% conversion of the cyclopropanecarboxamide in the first reaction zone. Preferably, the feed rates of the cyclopropanecarboxamide and the sodium hypochlorite are controlled to maintain a concentration of hypochlorite in the effluent of the first reaction zone of about 0.01 wt % up to about 0.02 wt %. At this concentration of hypochlorite, at least a 90% conversion of the cyclopropanecarboxamide of is achieved. The first reaction mixture from the first reaction zone is continuously removed and fed to a second reaction zone wherein the N-chlorocyclopropanecarboxamide and other intermediates, such as the corresponding cyclopropyl isocyanates and cyclopropyl carbamates, further react to form a second reaction mixture comprising an aqueous solution of a cyclopropylamine.

A variety of cyclopropanecarboxamides may be used as starting materials. Exemplary cyclopropanecarboxamides which may be used have the structure wherein $R^1$ and $R^2$ are independently selected from hydrogen, a linear or branched alkyl, alkenyl, or alkynyl radical containing up to about 6 carbon atoms. Examples of alkyl, alkenyl, and alkynyl groups include, but are not limited to, methyl, ethyl, n-propyl, isopropyl, isobutyl, n-butyl, tertiary butyl, pentyl, hexyl, vinyl, 1-propenyl, 3-butenyl, 2-pentenyl, 2-propynyl, 2-butynyl, 2-hexenyl, and various isomers thereof. The cyclopropanecarboxamide can be added as a melt, or more preferably as an aqueous solution. Cyclopropanecarboxamides typically are water soluble and their aqueous solutions can be generated in any concentration, especially if heated. In the present invention, cyclopropanecarboxamide concentrations in a range of about 5 wt % up to about 90 wt % in water are useful; however, concentrations in a range of about 10 wt % up to about 70 wt % are preferred, and a concentration range of about 15 wt % up to about 35 wt % is especially preferred.

It is convenient to premix the hypohalite and hydroxide solutions and thereby feed these reagents into the first reaction zone as a single aqueous solution. Within this solution, the preferred concentration range of alkaline hypohalite is about 10 wt % up to about 15 wt % and the concentration range. 5 of alkaline hydroxide is about 30 wt % up to about 50 wt %. The optimum molar ratio of hydroxide to hypohalite is in a range of about 2:1 to about 3:1 moles hydroxide:moles hypohalite. These ratios of hydroxide to hypohalite serve to stabilize hypohalite against decomposition and retard the formation of by-product cyclopropane acyl ureas. The preferred alkaline hypohalite is sodium hypochlorite and the preferred alkaline hydroxide is sodium hydroxide.

Our process is carried out wherein the temperature of first reaction zone is in a range of about 30° C. up to about 55° C. A more preferred temperature range for the first reaction zone is about 45° C. up to about 55° C. Within this temperature range, the reaction between the cyclopropanecarboxamide and the hypohalite react to give a first reaction mixture containing an N-halocyclopropanecarboxamide but may also contain cyclopropyl carbamates, trace amounts of cyclopropyl isocyanates, cyclopropylamines, and other non-identified intermediates and reaction by-products. Pressures in the range of about 0 kilopascals gauge up to about 2000 kilopascals gauge may be used as necessary to suppress boiling of the reaction mixture within the first reaction zone.

It is preferred that a tubular reactor, operated under substantially plug-flow conditions, i.e. conditions under which substantial backmixing of the reaction mixture is avoided, is used as the first reaction zone. While the dimensions of a plug flow reactor are a complex function of viscosity, flow rate, and diameter, the tubular reactor of the present invention preferably has a length:diameter ratio of at least 30:1. The tubular reactor may be operated under isothermal or adiabatic conditions; however, it is preferred that the reaction occur under substantially adiabatic conditions in which the temperature of the reaction is allowed to rise from the heat of reaction as the reaction proceeds.

The second reaction zone is maintained at a temperature range of about 60° C. up to about 150° C. with a more preferred range being from about 70° C. up to about 120° C. and a most preferred range being from about 70° C. up to about 105° C. The second reaction zone may be operated at a pressure range of about 0 up to about 2000 kilopascals gauge. Within this temperature range, the N-chlorocyclopropanecarboxamide and other intermediates, such as the corresponding isocyanates and carbamates, are converted to the corresponding amine. Heat may be added as necessary to maintain the temperature or, since the reaction is, very exothermic, the reaction may operate adiabatically. The retention time required in this reactor is dependent upon the operating temperature and concentration of reagents, but, generally, the time in this second reactor is about 5 minutes up to about 30 minutes. The pressure at which the second reaction zone is operated is not critical except it is desirable to employ sufficient pressure to maintain the desired temperature of the reaction mixture by suppressing vaporization of the reaction components. Although, various reactor types may be used for the second reaction zone, a continuous stirred tank reactor is the preferred format of the second reactor zone.

The process of the present invention may be illustrated with particular reference to a preferred embodiment wherein the concentration of sodium hypochlorite in the first reaction mixture is measured using UV-Visible spectroscopy and this measurement is used to control the rate of the cyclopropanecarboxamide and/or the sodium.hypochlorite feeds. Sodium hypochlorite is measured preferably at a wavelength of about 300 nm to about 375 nm and most preferably at wavelength of about 325 nm to 350 nm. The hypochlorite concentration in the first reaction mixture is controlled by feeding hypochlorite solution, either by itself or premixed with an alkaline hydroxide, into the first reaction zone until a response is detected in the desired range of the spectrum in the first reaction mixture as it exits from the first reaction zone. The preferred first reaction zone is a tubular reactor operated under substantially plug flow conditions. The first reaction zone is preferably maintained at a temperature in a range of about 30° C. up to about 55° C. and more preferably in a range of about 45° C. up to about 55° C. The hypochlorite feed rate is adjusted as needed to maintain preferably a concentration of hypochlorite in the range of about 0.01 wt % up to about 0.02 wt % in the effluent from the first reaction zone. At this level of hypochlorite, at least a 90% conversion of the cyclopropanecarboxamide is obtained.

The first reaction mixture is continuously introduced into a second reaction zone which is maintained at a higher temperature than the first reaction zone of about 60° C. up to about 150° C. with a more preferred range being from about 70° C. up to about 120° C. and a most preferred range being from about 70° C. up to about 105° C. At this higher range of temperatures, the first reaction mixture reacts further to produce a second reaction mixture in which a N-chlorocyclopropanecarboxamide and other intermediates, such as the corresponding isocyanates and carbamates, are converted to the corresponding cyclopropylamine. The preferred second reaction zone is a continuous stirred tank reactor. The second reaction mixture, comprising a cyclopropylamine, is continuously removed from the second reaction zone and may be introduced continuously into a distillation column for purification. The effluent may be introduced as a liquid stream or as mixture of liquid and vapor depending on the temperature and pressure of the second reaction zone and the distillation column. Typically, a distillation column containing about 5 equilibrium stages is sufficient to separate and purify the products. Although the effluent may be introduced at any stage within the distillation column, it is preferable to feed the effluent to an intermediate point in the distillation column, i.e. tray 10 in a 20 tray column. The distillation column may be heated by well-known external means (i.e., coils or tubes heated with steam, hot oil, etc.) or preferably by the injection of steam into the contents within the base of the distillation column. The cyclopropylamine is continuously removed from the top of the distillation column and waste products, comprising water, chloride and carbonate salts, unreacted cyclopropanecarboxamide, and higher boiling by-products, are continuously removed from base of the column.

Alternatively, the second-reaction zone may be omitted and the first reaction mixture may be removed from the first reaction zone and fed directly into the distillation column. In this embodiment, the conversion of the intermediate reaction products, e.g., N-chlorocyclopropanecarboxamides, cyclopropyl carbamates, and cyclopropyl isocyanates, to the cyclopropylamine product occurs concurrently with purification in the distillation column. Omitting the second reaction zone, however, requires greater distillation capacity to accomplish satisfactory purification of the cyclopropylamine, longer residence times in the distillation column, reduces separation efficiency, and generally leads to lower yields.

Mid-boiling impurities, i.e., impurities that boil at temperatures between that of the cyclopropylamine product and the base temperature of the distillation column, may be continuously removed by withdrawal through a sidedraw located near the middle of the column. These impurities, if allowed to accumulate, may eventually contaminate the cyclopropylamine product.

Figure 1:
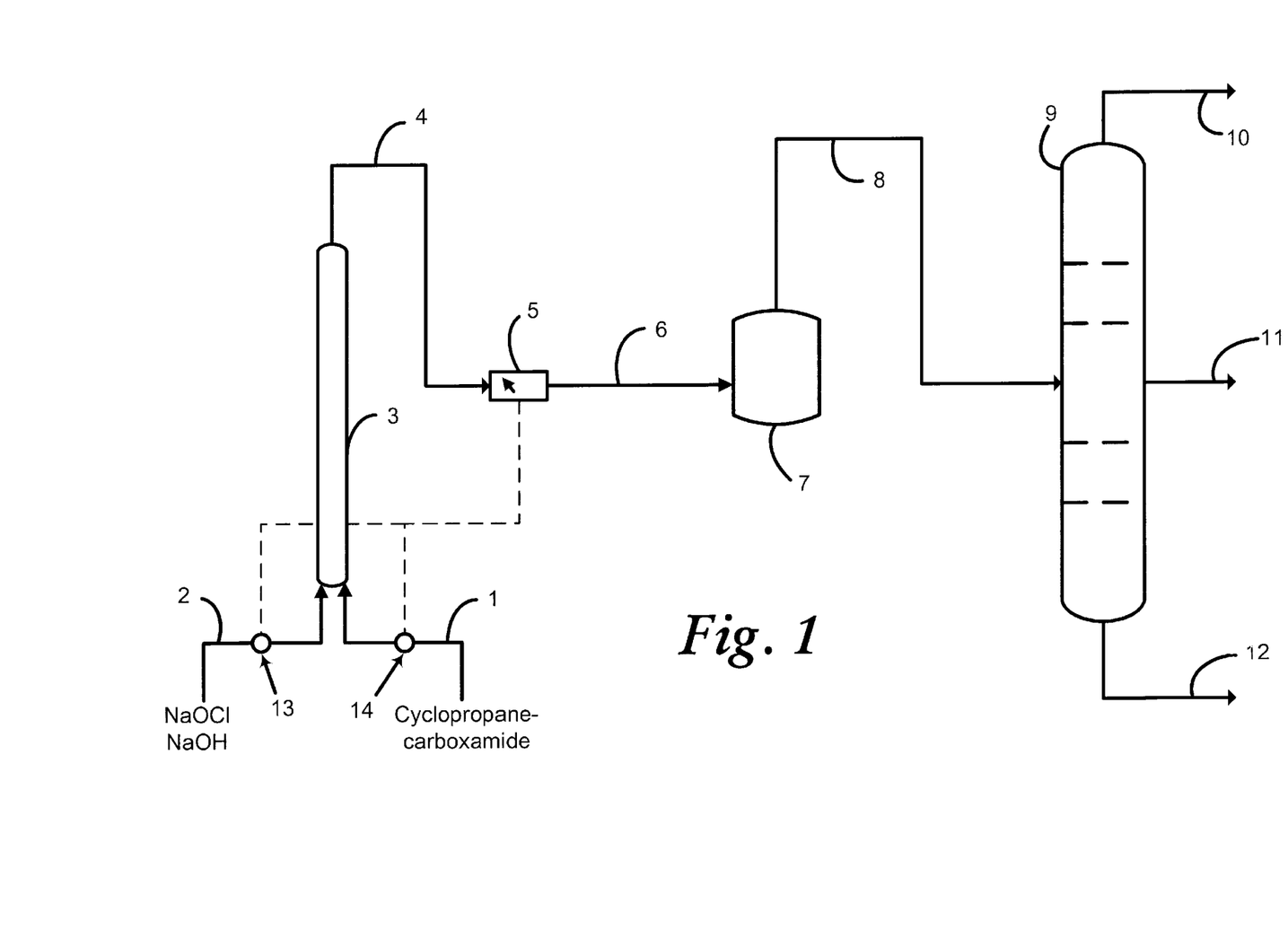
FIG. 1 is a block flow diagram illustrating a continuous process for the preparation of cyclopropylamine using 2 reaction zones, measurement of the reaction components in the first reaction mixture to control reactant feed rates, and purification of the cyclopropylamine product by continuous distillation.

A particularly preferred embodiment of the present invention is the continuous production of cyclopropylamine from cyclopropanecarboxamide and is illustrated by referring to the accompanying FIG. 1. An aqueous solution of cyclopropanecarboxamide and a solution of sodium hypochlorite and sodium hydroxide are fed into tubular reactor (3) through conduits (1) and (2) respectively to form a first reaction mixture comprising N-chlorocyclopropanecarboxamide. The first reaction mixture is removed continuously from reactor (3) through conduit (4), contacted with a UV-Visible spectrophotometric probe, and the concentration of hypochlorite is measured using a UV-Visible spectrophotometer (5). The measurement of the concentration of hypochlorite is used to control the feed rate of hypochlorite and/or carboxamide by controlling feed pumps (13) and (14), respectively. The effluent from reactor (3) is fed into a second reaction zone (7), comprising a continuous stirred tank reactor, through conduit (6) where the N-chlorocyclopropanecarboxamide and other intermediates react further to form a second reaction mixture comprising cyclopropylamine. The second reaction mixture is continuously removed from the reactor (7) and is introduced through conduit (8) into the middle of distillation column (9). Purified cyclopropylamine is removed from the top of the column through conduit (10). High-boiling impurities are removed from the base of the distillation column through conduit (12) and mid-boiling impurities are removed through sidedraw (11).

The process of the present invention is illustrated by the following example.

EXAMPLES

Example

An apparatus for the continuous production of cyclopropylamine was assembled by connecting the outlet of two variable speed peristaltic pumps (Cole-Parmer U-77912-00, Cole-Parmer, Vernon Hills, Ill.) using polytetrafluoroethylene (PTFE) flexible tubing (fitted with 4 mm PTFE tubing in the head of the reactor) to a mixer consisting of an 8 mm (⅜ in.) OD glass Y-shaped fittings into which a 2 mm stirbar was inserted and maintained in the junction of the "Y" and using 7.9 mm ID flexible tubing (L/S 17® C-FLEX® tubing, Cole-Parmer U-06424-25, Cole-Parmer, Vernon Hills, Ill.). The connection between the 4 mm PTFE tubing and 7.9 mm ID tubing was accomplished using a small section of 7.9 mm ID tubing as packing between the 4 mm PTFE tubing and the larger bore L/S 17 tubing. The mixer was stirred magnetically throughout the reaction and was connected to the first reactor using the minimum feasible length of 7.9 mm ID tubing. The first reactor, which represents a plug flow reactor, consists of a 19 cm long, 12 mm ID glass tube with 1) a thermocouple well at the entrance to the reactor occupying the first 3.5 cm of the reactor;
2) a 12 cm long jacketed section connected to circulating water bath;
3) a second 12 mm vacuum jacketed section; and
4) a section for a second thermowell for measuring the temperature at the exit and occupying the last 3.5 cm of the reactor.

The first reactor was followed by a UV-Visible cell that was constructed from corrosion resistant stainless steel (for example, HASTELLOY® alloy) and operated as a flowcell with ⅜ (9.5 mm) compression fittings at the exit and entrance to the reactor. The UV-Visible flowcell (monitor) was connected to the spectrometer via fiber optic cables to an UV-Visible fiber optic spectrophotometer with Xe lamp using a 2 meter UV fiber optic cables and a 10 mm pathlength flowcell. The spectrophotometer utilizes an optically stabilized light source (pulsed Xe for UV-Visible) and a 220–800 nm silicon diode array for UV/Visible. The connection to the reactor was accomplished by using a minimal section of ⅜ in. (9.5 mm) section of stainless steel tubing and connecting the tubing to the exit of the reactor using a short length of tubing sufficient to seal the space between the reactor and monitor (the space was minimized between the reactor and monitor). The exit of the UV-Visible flow cell was connected to a length of ⅜ (9.5 mm) of flexible PTFE tubing using a PTFE compression fitting.

The other end of the PTFE tubing was connected to a second glass reactor that was constructed in two pieces. The first piece consists of a male 24/40 standard taper joint to which a 4 cm length of ⅜ in. (9.5 mm) OD glass was connected to the top of the joint and a 12 cm long portion of ¼ in. (6.35 mm) OD glass tubing was connected to the bottom of the joint. The ⅜ in (9.5 mm) OD (inlet) side was joined to the flexible PTFE tubing using a PTFE compression fitting and was inserted into the second piece of the reactor which was constructed of a 15 cm long piece of tubing 41 mm OD glass with one sealed end and fitted with:

1) a sidearm located at 10 cm from the bottom of the tube and consisting of a 6 inch long piece of 10 mm glass tubing with a an 18/9 female ball joint fitted at the end tubing;

2) a curved thermocouple well placed a ca. 7–8 mm from the bottom of the closed end of the tube; and 3) fitted with a female 24/40 standard taper joint at the top.

The second reactor was sealed using the standard taper joint, placed with the base in a 60-watt base heater, and the sidearm connected to the feed plate of the distillation column. The distillation column consists of:

1) a base heater consisting of a 2 L round bottom flask equipped with an outlet for purging a portion of the base as needed and a 29/42 standard taper joint to fit the distillation column;

2) a 12 in. vacuum jacketed, silver lined column packed with corrosion resistant (MONEL® alloy) packing (PENN STATE® packing) and having 29/42 standard taper joints, 3) a feedplate with 29/42 standard taper joints (Kontes 532100-0028, Kimble/kontes, Vineland, N.J.);

4) a liquid side draw with 29/42 standard taper joints (deflammator) whose side draw was connected to a receiving vessel (consisting of 100 mL 24/40 standard taper round-bottomed flask) via a curved 18/9 ball joint to 24/40 standard taper joint with a nitrogen inlet;

5) a 12 in. vacuum jacketed, silver lined column packed with corrosion resistant (MONEL® alloy) packing (PENN STATE® packing) with 29/42 standard taper joints;

6) an automatic, liquid dividing, distilling head with 29/42 standard taper joints (Lab Glass LG-6171-100, Lab Glass, Vineland, N.J.) (which uses an external magnetic and timing device); and 7) a condenser with 29/42 standard taper joints and a drip tip.

Thermocouple wells were provided at the inlet and exit to the first (plug flow) reactor (thermocouple 1 and 2 respectively), the second reactor (thermocouple 3), the feed plate of the distillation column (thermcouple 4), the liquid sidedraw (thermocouple 5), the overhead take-off (distillation takeoff) (thermocouple 6), and in the base heater (thermocouple 7.) The portion of the apparatus extending from with the UV-Visible monitor to the distillation column inlet was insulated using insulating tape.

To feed the reactor, an NaOH/NaOCl solution was prepared by slowly adding 402 g of 50 wt % aqueous NaOH to 1418 g of 12.25 wt % aqueous sodium hypochlorite (by analysis) with constant cooling and stirring in an ice-water bath. An aqueous solution containing 17 wt % cyclopropanecarboxamide was prepared by dissolving 187 g (2.20 mol) of cyclopropanecarboxamide in 913 g of water. Each solution was fed separately using one of the two peristaltic pumps.

The reaction apparatus was first flushed with distilled water using both pumps until about 300–400 mL of water accumulates in the distillation base. The distillation base was then heated to reflux, the 60 watt base heater on the second reactor turned on to its maximum setting, and the circulating water bath set at 47° C. The UV-Visible spectrometer was turned on and spectra recorded every 5 minutes.

A flow of the 17 wt. % aqueous cyclopropanecarboxamide solution was established (measured addition rate: 0.372 moles cyclopropanecarboxamide/h) using the first pump. The second pump, feeding the NaOH/NaOCl solution was started and the addition of NaOH/NaOCl was carefully adjusted until the peak at 330 nm slowly oscillated between about 0.4 and about 1.1 absorbance units which corresponds to a NaOCl concentration of about 0.01 to about 0.02 wt %. When the feed rates were in balance, the rates of addition were 0.372 moles/h of cyclopropanecarboxamide and 0.377 mol/h sodium hypochlorite based on the initial analysis of the sodium hypochlorite solution.

The temperature at the outlet of the first. reactor was regulated between 51 and 54° C. by adjusting the temperature of the circulating oil bath. Once flow was established to the second reactor, the temperature rises rapidly and the output of 60 watt heater was lowered to about 20 watts. When the temperature of the overhead distillate drops to 49–54° C., the magnetic timer for the automatic, liquid dividing, distilling head was turned on using a 6:1 reflux ratio. Once the reagent addition rates were set using the UV-visible output and the temperatures at the outlet of the reactor and the overhead distillate were established, the reactor attained a steady state operation. The electrical output to the base heater required careful monitoring to keep the first column in the distillation train from flooding. At steady state, the operating temperatures as recorded at each thermocouple were:

| | |
|---|---|
| Thermocouple 1 - First (plug flow) reactor inlet: | 31–32° C. |
| Thermocouple 2 - First (plug flow) reactor outlet: (maintained by adjusting water jacket setting) | 51–54° C. |
| Thermocouple 3 - Second reactor: | 89–92° C. |
| Thermocouple 4 - Feed plate in distillation column: | 90–94° C. |
| Thermocouple 5 - Intermediate liquid take off: | 90–98° C. |
| Thermocouple 6 - Overhead takeoff (reflux ratio 6:1): | 49–54° C. |
| Thermocouple 7 - Distillation column base: | 100–103° C. |

The circulating water bath was adjusted between 47–48° C. as needed to maintain the exit temperature from the first reactor at about 51–52° C. The intermediate liquid takeoff (removed through a deflammator) was drained periodically as water insoluble material accumulated in the sample collection cup.

A total of 693.1 grams of an aqueous solution containing 17.0 wt % cyclopropanecarboxamide (equivalent to 117.8 g, 1.38 moles of cyclopropanecarboxamide) were delivered to the reactor, yielding 67.5 g (1.18 moles) of pure cyclopropylamine distillate (85% yield).

Comparative Example

This example demonstrates that lower yields are obtained when the spectroscopic control loop that was used in the previous example is omitted. Although an infrared spectroscopic probe and a UV probe was used to monitor the reaction in this example, the feeds to the reaction were not controlled from the spectroscopic measurements.

The apparatus was constructed by first fabricating a glass mixing section consisting of a water jacketed 90 mm long length of 19 mm OD tubing to which three inlets consisting of ¼ in (6.35 mm) OD glass tubing were placed vertically, at roughly equal distances. The bottom of the tube was sealed and a 24/40 standard taper female joint attached at the top. The isothermal plug flow reactor section consists of a water jacketed 24 in. (61 cm) long section of ⅝ in. (15.9 mm) ID glass tubing to which a 24/40 standard taper male joint was attached at the base. The top of the plug flow reactor was reduced to a ⅜ in. (9.5 mm) OD and the mixer and reactor section connected and sealed using the Rodavaris® joints. The mixer and reactor were both connected to a circulating constant temperature bath. During the course of the experiment, the temperature of the circulating water was maintained at a constant 25° C.

Using a sleeve of flexible ⅜ in. (9.5 mm) tubing (CFLEX Tubing L/S™ 35), the reactor was connected to an infrared sampling flowcell, which consists of a polytetrafluoroethylene block with ¼ in. (6.35 mm) bore and ⅜ in. (9.5 mm) inlets and outlets. An inlet was tapped into the side of the polytetrafluoroethylene block to accommodate a ⅝ in. (1.6 cm) compression fitting. Into this side inlet was inserted a attenuated total reflectance probe (DICOMP™ ASI Applied Systems, a Mettler-Toledo AutoChem Co., Millersville, Md.) using ⅝ in. (1.6 cm) male polytetrafluoroethylene compression fitting with a polytetrafluoroethylene ferrule to create a seal between the reflectance probe and the polytetrafluoroethylene block. The, attenuated total reflectance probe was connected to a mid-infrared spectrometer (REACTIR™ 1000, ASI Applied Systems, a Mettler-Toledo Co., Millersville, Md.).

The exit of the infrared sampling port was connected to a UV-Visible cell that was constructed from corrosion resistant stainless steel (for example, HASTELLOY® alloy) and operated as a flowcell with ⅜ in. (9.5 mm) compression fittings at the exit and entrance to the reactor. The UV-Visible flowcell was connected to the. spectrometer via fiber optic cables to an UV-Visible fiber optic spectrophotometer (OPTICAL SOLUTIONS® spectrophotometer) with a Xe lamp using a 2 meter UV fiber optic cables and a 10 mm pathlength flowcell. The spectrophotometer utilizes a optically stabilized 220–800 nm Silicon diode array for a UV/Visible light source (pulsed Xe for UV-Visible). The connection to the reactor was accomplished by using a minimal section of ⅜ in. (9.5 mm) section of stainless steel tubing and connecting the tubing to the exit of the reactor using a short length of flexible tubing sufficient to seal the space between the reactor and monitor.

The second reactor consists of a jacketed 6 inch (15.2 cm) length of 1 in. (25 mm) OD glass tube which was sealed at the bottom and jacketed to a height of 4 in. (10 cm). A female 24/40 standard taper glass joint was fitted to the top of the reactor. Between the glass joint and the jacketed section, was placed a sidedraw, consisting of 6 inch (15.2 cm) length of ½ in. (12.5 mm) with a 18/9 standard female ground glass ball joint. To facilitate drainage down the side arm, the sidedraw tube was placed at a 75° angle to the jacketed section of the tube. A stirbar was placed in the second reactor. Using a polytetrafluoroethylene 24/40 male standard taper thermometer adapter (Lab Glass Cat. No. LG 10447T-406, Lab Glass, Vineland, N.J.), a section of ⅜ in (9.5 mm) OD glass tubing was inserted to a length just long enough to clear the stirbar when inserted into the second reactor. The reactor was sealed and the inlet of the ⅜ in. (9.5 mm) OD glass tubing was connected to the outlet of the UV-Visible flowcell via a length of ⅜ in. (9.5 mm ID) flexible tubing. When operating the apparatus, steam was fed continuously into the second reactor jacket.

The outlet of the second reactor was connected to a distillation apparatus. The distillation column consisted of:

1) a base heater consisting of a 3 L round bottom flask equipped with an outlet for purging a portion of the base as needed and a 29/42 standard taper joint to fit the distillation column;
2) a 20 plate vacuum jacketed, silver lined Oldershaw column with 29/42 standard taper joints (Lab Glass Cat. No. LG-5631-106, Lab Glass, Vineland, N.J.);
3) a feedplate with, 29/42 standard taper joints (Kontes 532100-0028, Kimble Kontes, Vineland, N.J.);
4) a 20 plate vacuum jacketed, silver lined Oldershaw column with 29/42 standard taper joints (Lab Glass Cat. No. LG-5631-106, Lab Glass, Vineland, N.J.);
5) an automatic, liquid dividing, distilling head with 29/42 standard taper joints (Lab Glass LG-6171-100, Lab Glass, Vineland, N.J.) (which uses an external magnetic and timing device); and
6) a condenser with 29/42 standard taper joints and a drip tip. Thermocouple wells were provided in the feed plate of the distillation column (thermcouple 1), the overhead take-off (distillation takeoff) (thermocouple 2), and in the base heater (thermocouple 3).

To feed the reactor, an NaOH/NaOCl solution was prepared by slowly adding 434.8 g of 50 wt. % aqueous NaOH to 1533 g of 12.02 wt % aqueous sodium hypochlorite (by analysis) with constant chilling and stirring in an ice-water bath. A cyclopropanecarboxamide solution was prepared by dissolving 187 g (2.20 mol) of cyclopropanecarboxamide in 913 g of water to produce a 17 wt. % solution of cyclopropanecarboxamide.

Two variable speed peristaltic polytetrafluoroethylene (PTFE) tubing pumps (Cole-Parmer U-77912-00, Cole-Parmer, Vernon Hills, Ill.), fitted with 4 mm PTFE tubing in the head of the pump were connected to the base of the mixer and highest inlet of the mixer using PTFE compression fittings. The cyclopropanecarboxamide was fed through the pump feeding the top of the mixer and the largest portion of the NaOH/NaOCl solution was fed through the lowest inlet of the mixing section using the pump connected to the base of the mixer.

A peristaltic pump (Microflex C/L, Cole-Parmer Cat. No. U-77120-20, Cole Parmer, Vernon Hills, Ill.) fitted with 1.46 mm microbore flexible tubing was connected to the middle inlet of the mixer, using an adapter consisting of a 1 mm OD capillary fitted to a piece of ¼ in. (6.35 mm) OD tubing. The adapter was carefully inserted into the capillary tubing and the connection between the mixer and adapter was accomplished using a small section of ¼ in. (6.35 mm ID) flexible tubing. The inlet was submersed in the NaOH/NaOCl solution and this pump was used to finely adjust the addition of NaOH/NaOCl.

To operate the apparatus, about 400–500 mL of water were added to the base of the distillation base. The distillation base was then heated to reflux, the stirrers for both the mixer and second reactor were started, the steam feed was started on the reactor, and the circulating water bath, which was set at 25° C., was started. After all the parts of the apparatus were warm, the mixer was filled with NaOH/NaOCl using both the pumps. As soon the mixer was full, the addition of 17% aqueous cyclopropanecarboxamide solution, which was preset at an addition rate of 4.2 mL/min (4.15 g solution/min or 0.706 g cyclopropanecarboxamide/min), was started. This addition rate of the cyclopropanecarboxamide and NaOH/NaOCl solutions was maintained until a consistent response was obtained in both the IR and UV-Visible detectors. This takes about 15–25 minutes. Actual addition rates were determined gravimetrically by periodically measuring the decrease in the weight of the feed solutions.

The addition rate of the NaOH/NaOCl solution was varied using several different NaOCl:cyclopropanecarboxamide molar ratios ranging from 0.84 to 1.07, monitoring the response of the UV-Visible detector at 330 nm and the IR response at 934 cm$^{-1}$ (a cyclopropanecarboxamide peak), and waiting 25 minutes between changes for the reactor system to reach steady state. At ratios up to 0.94, the UV-Visible detector showed no response, but at ratios as low as 1.01, representing just a 1% molar excess of NaOCl, the detector showed responses >1.4 absorbance units.

The IR response was less sensitive, with a gradually decreasing absorbance (dropping from 0.08 absorbance units to 0.03 absorbance units as the ratio was increased from 0.84 to 0.94. The response gradually falls to 0 absorbance units as the NaOCl:cyclopropanecarboxamide ratio was further increased to 1.01.) The UV-Visible spectrophotometer is the preferred instrument for measuring the hypochlorite concentration because of its higher sensitivity over infrared spectroscopy.

The distillation column was operated throughout this process using a reflux ratio of 6:1 and draining the base as necessary. The yield of cyclopropylamine was 62%.

We claim:

1. Continuous process for the preparation of amines which comprises the steps of:
   I. continuously feeding a carboxamide reactant, an aqueous alkaline hypohalite reactant, and an aqueous alkaline hydroxide reactant to a first reaction zone wherein the carboxamide, hypohalite, and hydroxide react to form a first reaction mixture comprising a plurality of components wherein at least one of the components is an N-halo-carboxamide;
   II. continuously removing the first reaction mixture from the first reaction zone;
   III. measuring the concentration of at least one component of the first reaction mixture and using the result of that measurement to control the feed rate of at least one of the reactants of step I to achieve at least 90% conversion of the carboxamide in the first reaction zone; and
   IV. continuously feeding the first reaction mixture to a second reaction zone wherein the first reaction mixture further reacts to form a second reaction mixture comprising an aqueous solution of an amine.

2. Process according to claim 1 wherein the carboxamide of Step I has the structure:

wherein R is (i) a linear or branched alkyl, alkenyl, or alkynyl radical containing up to about 10 carbon atoms, (ii) a cycloalkyl or cycloalkenyl radical containing 3 to about 7 carbon atoms, (iii) a carbocyclic aromatic or heterocyclic aromatic radical which may carry one or more substituents, or (iv) a 5- or 6-membered non-aromatic heterocyclic radical comprising one or more hetero atoms selected from the group consisting of oxygen, nitrogen, phosphorus, and sulfur.

3. Process according to claim 2 wherein the carboxamide of Step I is about 5 wt % to about 90 wt % carboxamide in water, the aqueous alkaline hypohalite of Step I is about 3 wt % to about 17 wt % hypohalite, and the aqueous alkaline hydroxide of Step I is about 10 wt % to about 50 wt % alkaline hydroxide.

4. Process according to claim 3 wherein the alkaline hypohalite is selected from the group consisting of lithium hypochlorite, lithium hypobromite, sodium hypochlorite, sodium hypobromite, potassium hypochlorite, potassium hypobromite, calcium hypochlorite, and calcium hypobromite; and the alkaline metal hydroxide is selected from the group consisting of lithium hydroxide, sodium hydroxide, potassium hydroxide, and calcium hydroxide.

5. Process according to claim 4 wherein the molar ratio of alkaline hypohalite to alkaline hydroxide fed to the first reaction zone is about 2:1 moles hypohalite:moles hydroxide.

6. Process according to claim 5 wherein the first reaction zone is maintained at a temperature of about 30° C. up to about 55° C. and a pressure of about 0 kilopascals up to about 2000 kilopascals gauge, and the second reaction zone is maintained at a temperature of about 60° C. up to about 150° C. and a pressure of about 0 kilopascals up to about 2000 kilopascals gauge.

7. Process according to claim 6 wherein the first reaction zone is a tubular reactor.

8. Process according to claim 7 wherein the measurement of reaction component concentrations of Step IV is carried out using UV-Visible spectroscopy, infrared spectroscopy, or a combination of UV-Visible and infrared spectroscopy.

9. A continuous process for the preparation of cyclopropylamines which comprises the steps of:
   I. continuously feeding (i) an aqueous solution of a cyclopropanecarboxamide and (ii) a solution comprising sodium hypochlorite and sodium hydroxide to a first reaction zone comprising a tubular reactor, wherein the cyclopropanecarboxamide, sodium hypochlorite, and sodium hydroxide react to form a first reaction mixture comprising an N-chlorocyclopropanecarboxamide;
   II. continuously removing the first reaction mixture from the first reaction zone;
   III. measuring the concentration of sodium hypochlorite in the first reaction mixture using UV-Visible spectroscopy and using the result of that measurement to control the feed rate of at least one of the solutions (i) or (ii) of Step I to achieve at least 90% conversion of the cyclopropanecarboxamide in the first reaction zone; and
   IV. continuously feeding the first reaction mixture from the first reaction zone to a second reaction zone wherein the first reaction mixture further reacts to form a second reaction mixture comprising an aqueous solution of a cyclopropylamine.

10. Process according to claim 9 wherein the feed rate of at least one of the solutions (i) or (ii) in Step III is controlled to maintain a concentration of hypochlorite of about 0.01 wt % up to about 0.02 wt % in the first reaction mixture.

11. Process according to claim 10 wherein the cyclopropanecarboxamide has the structure:

wherein $R^1$ and $R^2$ are independently selected from hydrogen, a linear or branched alkyl, alkenyl, or alkynyl radical containing up to about 6 carbon atoms.

12. Process according to claim 11 wherein the aqueous solution (i) of Step I is about 15 wt % up to about 55 wt % cyclopropanecarboxamide and the solution (ii) of Step I is about 7 up to about 15 wt % sodium hypochlorite and about 30 up to about 50 wt % sodium hydroxide.

13. Process according to claim 12 wherein the molar ratio of sodium hydroxide to sodium hypochlorite in feed solution (ii) of Step I is about 2:1 up to about 3:1 moles hydroxide:moles hypochlorite.

14. Process according to claim 13 wherein the first reaction zone is maintained at a temperature of about 45° C. up to about 55° C. and a pressure of about 0 kilopascals up to about 2000 kilopascals gauge, and the second reaction zone is maintained at a temperature of about 70° C. up to about 105° C. and a pressure of about 0 kilopascals up to about 2000 kilopascals gauge.

15. Process according to claim 14 wherein the tubular reactor of Step I has a length to diameter ratio of at least 30:1 and is operated under substantially adiabatic conditions.

16. Process according to claim 15 wherein the second reaction mixture is continuously fed into a distillation column having a top, middle, and base section.

17. Process according to claim 16 wherein a first distillate comprising the cyclopropylamine is continuously removed from the top section of the distillation column and a second distillate comprising mid-boiling organic impurities is continuously removed from the middle section of the distillation column.

18. Process according to claim 17 wherein $R^1$ and $R^2$ are hydrogen.

* * * * *